(12) United States Patent
Spedden (10) Patent No.: US 8,101,274 B2
(45) Date of Patent: Jan. 24, 2012

(54) SOLID STATE MEMBRANES WITH SURFACE-EMBEDDED GLYCOSYLATED AMPHIPHILIC MOLECULES AND MICELLES FORMED THEREFROM

(76) Inventor: Richard H. Spedden, Clarksville, MD (US)

( * ) Notice: Subject to any disclaimer, the term of this patent is extended or adjusted under 35 U.S.C. 154(b) by 1240 days.

(21) Appl. No.: 11/761,045

(22) Filed: Jun. 11, 2007

(65) Prior Publication Data

US 2008/0305348 A1    Dec. 11, 2008

(51) Int. Cl.
  *B32B 9/04*    (2006.01)
  *B01D 3/00*    (2006.01)
  *B01D 15/04*   (2006.01)
  *B01D 17/00*   (2006.01)

(52) U.S. Cl. .................. 428/411.1; 210/633; 210/638; 210/643

(58) Field of Classification Search .................. None
  See application file for complete search history.

(56) References Cited

U.S. PATENT DOCUMENTS

| | | |
|---|---|---|
| 4,886,604 A | 12/1989 | Sleytr et al. |
| 5,188,837 A | 2/1993 | Domb et al. |
| 5,221,535 A | 6/1993 | Domb |
| 5,227,165 A | 7/1993 | Domb et al. |
| 5,340,588 A | 8/1994 | Domb |
| 5,780,062 A | 7/1998 | Frank et al. |
| 5,824,337 A | 10/1998 | Mullen |
| 6,284,267 B1 | 9/2001 | Aneja |
| 6,284,375 B1 | 9/2001 | Jin et al. |
| 6,395,302 B1 | 5/2002 | Hennink et al. |
| 6,528,092 B2 * | 3/2003 | Mullen .................. 424/489 |
| 6,835,394 B1 | 12/2004 | Discher et al. |
| 6,884,842 B2 | 4/2005 | Soane et al. |
| 7,052,719 B2 | 5/2006 | Bernstein et al. |
| 7,148,031 B2 | 12/2006 | Mullen |
| 2001/0000470 A1 | 4/2001 | Bernstein et al. |
| 2002/0048604 A1 | 4/2002 | Mullen |
| 2003/0171558 A1 | 9/2003 | Kadiyala et al. |
| 2003/0235619 A1 | 12/2003 | Allen et al. |
| 2004/0052836 A1 | 3/2004 | Li et al. |
| 2005/0048110 A1 | 3/2005 | Discher et al. |
| 2005/0158389 A1 | 7/2005 | Domb |
| 2005/0180922 A1 | 8/2005 | Discher et al. |
| 2005/0244425 A1 | 11/2005 | McKee et al. |
| 2005/0275123 A1 | 12/2005 | Chopra et al. |
| 2006/0003387 A1 | 1/2006 | Peelle et al. |
| 2006/0057192 A1 | 3/2006 | Kane |
| 2006/0127950 A1 | 6/2006 | Bosques et al. |
| 2006/0177495 A1 | 8/2006 | Allen et al. |
| 2006/0205639 A1 | 9/2006 | Domb et al. |
| 2007/0037933 A1 | 2/2007 | Kurth et al. |
| 2007/0224640 A1 * | 9/2007 | Caldwell et al. ............ 435/7.1 |

FOREIGN PATENT DOCUMENTS

WO    WO91/07171 A1    5/1991

* cited by examiner

*Primary Examiner* — Sheeba Ahmed (57) ABSTRACT

Disclosed herein are glycosylated amphiphilic molecules composed of hydrophobic "tails" and hydrophilic "heads" that self align to form a membrane at the interface of a polar solvent and a non-polar liquid or a solid. The present invention is directed to a solid state membrane, typically a thin film, composed of a non-polar solid material having the hydrophobic "tail" of a glycosylated amphiphilic molecule embedded in or linked to its surface such that the hydrophilic "head" protrudes from the solid surface and presents useful properties to the surrounding environment. A membrane or film in accordance with the present invention is produced when a non-polar liquid, in the presence of a polar solvent and an amphiphilic biological compound, undergoes a transformation from liquid to solid, through thermal, chemical or radiative means, with the resultant effect that the amphiphilic molecule is affixed or "locked" to the surface, more particularly the hydrophobic ends of the amphiphilic compounds are mechanically or chemically linked to or embedded in the non-polar solid. The membrane and micelles produced therefrom remain stable even in the absence of the polar solvent, thereby allowing the hydrophilic components of the amphiphilic compounds to present useful properties at the surface thereof.

13 Claims, 4 Drawing Sheets

SOLID STATE MEMBRANES WITH SURFACE-EMBEDDED GLYCOSYLATED AMPHIPHILIC MOLECULES AND MICELLES FORMED THEREFROM

FIELD OF THE INVENTION

The present invention relates to the field of solid state glycosylated amphiphilic membranes and micelles formed therefrom. More particularly, the present invention relates to solid films or membranes formed from the spontaneous aggregation and specific alignment of glycosylated amphiphilic molecules, at the interface between a polar solvent, typically water, and a non-polar liquid, often a lipid. In the context of the instant invention, the hydrophilic "head" end of the amphiphilic molecule preferably exhibits useful biological properties while the hydrophobic "tail" end is sufficiently hydrophobic and/or lipophilic so as to enable micelle formation.

BACKGROUND OF THE INVENTION

Amphiphilic molecules with both hydrophobic and hydrophilic ends tend to self align to form a membrane at the interface of a polar solvent and a non-polar liquid or a solid. When the amphiphilic molecules are in the presence of a polar solvent and a non-polar liquid, they form micelles or micelle-like structures in which the hydrophobic end of the molecule is embedded in the non-polar liquid. When the amphiphilic molecules are in the presence of a polar solvent and a solid, the hydrophobic ends of the amphiphilic compound tend to align against the solid with the hydrophilic end presented to the solvent. In both these situations, when the polar solvent is removed, the electrical forces which maintain the alignment of the amphiphilic compounds are also removed and the membrane structure fails.

These types of structures, often referred to interchangeably as micelles, liposomes or vesicles, are well known in science and nature. For example, biological cell membranes consist of lipid bilayers in which amphiphilic phospholipids and related compounds align with their hydrophobic ends against a lipid layer and their hydrophilic ends facing surrounding or interior sides of the membrane; the resultant construct is a double wall of phospholipids.

A useful rendition of these structures in conjunction with non-polar liquids has been achieved through the use of biological amphiphilic compounds to form micelles and micelle-like structures. In particular, lipo-glycoprotein membranes and micelles formed therefrom are described in U.S. Pat. Nos. 5,824,337, 6,528,092 and 7,148,031, all to Elaine Mullen, the entire contents of which are incorporated herein by reference. In these patents, the unique and important contribution of Mullen in the creation of the lipo-glycoprotein membranes over other micelle-like constructs is the presentation of important glycans and other biological structures at the surface of the membrane in a manner that can be beneficially used. The presence of these glycans allows for the transport of substances that can be dissolved or suspended in lipids as well as the capture and concentration of biological and inorganic entities that naturally bind to the selected glycan structures.

Amphiphilic compounds have been used in the emulsion polymerization process to produce synthetic rubber and some grades of plastics (PVC, polystyrene, PMMA, polyvinylidene fluoride and PTFE). The emulsion polymerization process is designed to produce small polymer particles that can remain in suspension in products such as paint or other emulsions.

Previous work done in the field combining polymer substrata with biological amphiphilic compounds at the surface has been focused on production of micelle-like structures, without attention to preserving or utilizing biological surface properties of any surfactants used. The present invention is intended to overcome disadvantages and deficiencies of the prior art, particularly as it pertains to long term storage and facilitated transport.

SUMMARY OF THE INVENTION

Accordingly, it is an objective of the present invention to provide a non-polar solid surface or film, for example of a polymer, plastic or wax, that has embedded in it or conjugated or chemically bound to it the hydrophobic end(s) of a glycosylated amphiphilic molecule, such that its opposing hydrophilic end(s) having useful functional properties are expressed at or above the surface of the solid. These properties may be viable either in air or when a polar solvent, such as water, is present.

The present invention is useful in imbuing various surface properties of organic cells onto the surface of solid materials.

The present invention represents an improvement in the art that utilized similar membranes formed between a polar solvent and a non-polar liquid. Structures of such membranes traditionally include micelles and liposomes wherein the hydrophobic groups align at the interface between a polar solvent and a non-polar liquid. The solid state films of the present invention differ from conventional micelles and liposomes in that the hydrophobic groups are affixed to or anchored in a solid in such a way that the properties of the hydrophilic groups are preserved on the surface for advantageous use. In conventional membranes between a polar solvent and a non-polar liquid, if the polar solvent is removed, the alignment of the hydrophobic and hydrophilic ends of the amphiphilic compounds fails and the membrane is destroyed. However, with the solid state films of the present invention, the polar solvent can be removed and then later reintroduced or then another polar solvent introduced with maintenance of the properties of the hydrophilic groups on the surface.

It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

Accordingly, it is an object of the present invention to provide a solid state film having at least one functionally active surface, the film composed of a non-polar substrate having a homogenous or heterogenous population of glycosylated amphiphilic molecules affixed thereto, each glycosylated amphiphilic molecule composed of a hydrophobic tail end and a hydrophilic head end provided with one or more functional groups such that the hydrophobic tail ends are embedded in or chemically or mechanically linked to the non-polar substrate and the functional groups of the hydrophilic tail ends project from the substrate so as to provide at least one surface of said film with functional activity.

It is a further object of the present invention to provide a solid state micelle or micelle-like structure with a surface film of the present invention, wherein the non-polar substrate and hydrophobic tail ends are sequestered in the interior of the micelle while the hydrophilic head ends are present on the outer surface of the micelle.

It is yet a further object of the present invention to provide a method for making a film of the present invention, including the following steps:
  (a) providing a polar solvent having sufficient quantities of one or more glycosylated amphiphilic molecules dissolved therein;
  (b) exposing the polar solvent to a non-polar liquid, the non-polar liquid being immiscible in the polar solvent;
  (c) allowing the glycosylated amphiphilic molecules to align so as to form a membrane that separates the polar solvent from the non-polar liquid; and
  (d) inducing transformation of the non-polar liquid to a corresponding non-polar solid having upper and lower surfaces, wherein the hydrophobic tail ends of the amphiphilic molecule are embedded in or chemically or mechanically linked to the upper surface of the non-polar substrate and the hydrophilic tail ends project from the upper surface into the polar solvent so as to yield a film having functional activity.

It is a further object of the present invention to provide a method of extracting a target molecule of interest from a sample, including the following steps:
  (a) exposing the sample to a solid state membrane of the instant invention, wherein the functional groups present at the hydrophilic tail end of the glycosylated amphiphilic molecules have a binding affinity for a target molecule;
  (b) allowing sufficient time for the functional groups to bind target molecules present in the sample; and
  (c) removing or separating the membrane, to which the target molecules are bound, from the sample.

It is yet another object of the present invention to provide a method of enhancing the biocompatibility of a medical device including the step of coating a solid state membrane of the present invention onto one or more exposed surfaces of the device. Medical devices having such membrane coatings are also provided herein.

It is a further object of the present invention to provide economical solid surfaces which can be imbued with useful properties of glycosylated amphiphilic compounds such as glycoproteins. Such surfaces are important in the fields of glycomics and proteomics for the study of how sugars and proteins react with various biological compounds. The surfaces are also useful in the field of pathogen capture, concentration and detection. Such surfaces capture the pathogen by presenting the same or similar sugars that the specific pathogen, etc. binds to in the body. A surface with this characteristic can concentrate the pathogen to a point where it can be detected through conventional detection means. Accordingly, it is an object of the present invention to utilize the glycosylated amphiphilic membranes of the present invention, in the form of a solid surface film or a film coating, to isolate and extract target compounds from a particular environment or sample.

It is a further object of the present invention to provide compositions and methods for preventing an immune response in a mammal. In that vein, it is an object of the present invention to utilize the glycosylated amphiphilic membranes of the present invention in the fabrication of or as a film coating for artificial organs, implants, and transplant materials, including both living and nonliving tissue. It is well-accepted that a material that mimics the surface properties of a biological cell or tissue is less likely to generate an immune response. Accordingly, through the selection of an appropriate biocompatible glycosylated amphiphile, one can provide a biomimetic membrane which would be useful in the formation of or as a film coating for various body contacting, penetrating or implanted devices. Such glycosylated amphiphilic membranes of the present invention, embedded with molecules that mimic biological molecules or express a variety of biological properties, can also prove useful in wound dressings and drug delivery.

Within the context of biocompatibility, the use of lipids and waxes from a biocompatible entity as the non-polar substrate is anticipated as a means to further insure compatibility or achieve synergistic benefits. For example, the non-polar substrate may comprise a natural wax or fat isolated from an antigen-matched human donor.

These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art having knowledge of various amphiphilic compounds, self-assembly techniques and peptide synthesis. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF THE DRAWINGS

Various aspects and applications of the present invention will become apparent to the skilled artisan upon consideration of the brief description of the figures and the detailed description of the present invention and its preferred embodiments which follows:

FIG. 1 depicts a classic micelle structure, in which the hydrophilic "head" regions present outward to contact the surrounding solvent while the hydrophobic "tail" regions are sequestered in the micelle centre.

FIG. 2 is a schematic of a glycoprotein micelle of the present invention, particularly depicting the spontaneous aggregation and specific alignment of glycoproteins to form a membrane at the interface between polar and non-polar solutions.

FIG. 3 depicts the successful binding of lectins to the sugars of the glycoproteins presented on the surface of the paraffin micelles of Example 1.

FIG. 4 depicts the successful binding of *Salmonella* to the sugars of the glycoproteins presented on the surface of the wax micelles of Example 5.

DETAILED DESCRIPTION OF THE PREFERRED EMBODIMENTS

This present invention constitutes a marked improvement in the area of micelle technology, particularly those wherein the hydrophobic materials are lipids or lipid-like structures or wherein the amphiphilic compounds surround a solid material but are not bound to that solid material. In such manifestations of micelles, if the surrounding solvent is removed, the micelle structure fails and the advantages derived from a surface that is presenting glycans or other useful biological materials is lost.

Although any methods and materials similar or equivalent to those described herein can be used in the practice or testing of embodiments of the present invention, the preferred methods, devices, and materials are now described. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the present invention, the following definitions apply:

As used herein and in the appended claims, the singular forms "a", "an" and "the" include plural reference unless the context clearly dictates otherwise. Thus, for example, reference to a "molecule" is a reference to one or more molecules and equivalents thereof known to those skilled in the art, and so forth.

I. Elements of the Present Invention

The present invention is directed, at least in part, to a solid state film composed of a non-polar substrate having a surface to which a plurality of glycosylated amphiphilic molecules are adhered or affixed.

In the context of the present invention, the terms "film" and "membrane" are used interchangeably to refer to the thin (usually a molecule in depth), wall-like structure formed by the specific alignment of amphiphilic molecules in the presence of polar and non-polar media. The film or membrane of the present invention can consist of a mixture of different amphiphilic molecules. Within the concept of this invention, the membrane can assume any form that the interface between polar and non-polar media can assume, including curved of any radius (including constant and irregular radius (rough) spheres), flat or a random combination (rough) surfaces. The important property is that once the non-polar media is transformed to its solid state the hydrophobic ends of the amphiphilic molecules or the matrix that the molecules form become affixed to the solid's surface while the hydrophilic ends remain free. Mullen micelles can be formed in the manner taught in the relevant Mullen patents while the non-polar media is in a liquid state. Rapid cooling preserves the micelle form in the transition of the non-polar media to a solid state.

As used herein and in the appended claims, the term "non-polar" refers to a substance that is relatively uncharged, typically water insoluble (hydrophobic). In the context of the present invention, the non-polar substrate must be capable of stable expression both as a liquid and a solid. In preferred embodiments, the non-polar substrate exists in solid state at a conventional room temperature (typically between 15 and 25° C.). However, bearing in mind that thermal degradation of many amphiphilic compounds is a function of time at elevated temperature and that the non-polar substrate needs to be in a liquid state for only a very short period of time to permit the hydrophobic tails of the amphiphilic compound to become bound in the surface, relatively high processing temperatures can indeed be used without causing substantial degradation of the amphiphilic compound.

Furthermore, in that pressure and temperature are inversely related, non-polar substrates with melting points above the boiling point of the desired polar solvent can be used if the films are formed while the liquids are under pressure. Examples of non-polar materials suitable for use in the context of the instant invention include, but are not limited to, resins, synthetic and natural waxes, synthetic plastics, polymers, and copolymers, including elastic, thermoplastic and vinyl polymers, nylons, polytheylenes and the like. Any mixture of hydrocarbons that results in a non-polar liquid when heated and become solid or semi-solid when cooled are appropriate. Waxes such paraffin, carnauba, beeswax, candelilla, ceresine, ozokerite, and various other animal, vegetable, and synthetic waxes and blends thereof are particularly suitable for use in the instant invention. Petroleum jelly and many animal and vegetable fats are other examples of appropriate non-polar substrate materials.

As used herein and in the appended claims, the term "amphiphilic" describes any of many organic and synthetic molecules that possess both hydrophilic and hydrophobic properties. It is used interchangeably herein with the term "amphipathic" to describe molecules that have a polar end that is attracted to water and a non-polar end that is repelled by it. Amphiphilic compounds suitable for use in the context of the instant invention may express a net charge at physiological pH, either a net positive or negative net charge, or may be zwitterionic.

The hydrophobic component of an amphiphilic molecule is typically a large hydrocarbon moiety, such as a long chain of the form $CH_3(CH_2)_n$, with n>4. The hydrophilic component is either comprised of charged groups (e.g., anionic entities such as carboxylates, sulfates, sulfonates, and phosphates, or cationic entities such as amines, amino acids, or peptides) or polar groups such as alcohols. Often, amphiphilic species have several hydrophobic parts, several hydrophilic parts, or several of both. Proteins and some block copolymers are such examples. The present invention includes both glycosylated biological amphiphiles and glycosylated synthetic molecules, such as block copolymers. Illustrative methods for preparing glycosylated block copolymers are disclosed in U.S. Pat. No. 7,109,280 (Kulkarni, et. al.), the entire contents of which are incorporated by reference herein. Block copolymers can be used to construct a hydrophobic tail with the same functionality as the hydrophobic amine based tails of glycoproteins.

Surfactants such as sodium dodecyl sulphate, benzalkonium chloride, octanol, and cocaminopropyl betaine are examples of amphiphilic compounds with known industrial uses. However, as noted above, the present invention is directed to glycosylated amphiphiles, examples of which include, but are not limited to, glycoproteins, glycolipids, glycosylated block copolymers and the like. As used herein, the term "glycosylation" refers to the addition of a carbohydrate moiety, typically a sugar, to either a biological molecule or a biocompatible synthetic molecule, such as a block copolymer. In the former context, glycosylation frequently arises as a result of co-translational or post-translational modification. In the latter context, the glycosylating moiety is frequently selected for its ability to mimic the surface properties of a biological cell or tissue and, in turn, reduce the immunogenic character of the block copolymer.

In the context of the present invention, a glycosylated lipid (or "glycolipid") is a biological molecule composed of a lipid and a carbohydrate, typically an oligosaccharide, whereas a glycosylated protein (or "glycoprotein") is a biological molecule composed of a protein and an oligosaccharide. In the context of glycoproteins, the addition of sugar chains to a protein occurs either at an asparagine moiety (referred to herein and elsewhere in the art as "N-glycosylation") or at a hydroxylysine, hydroxyproline, serine or threonine moiety (referred to herein and elsewhere in the art as "O-glycosylation"). In the context of the present invention, N-linked glycoproteins are more preferred.

Monosaccharides commonly found in eukaryotic glycoproteins include glucose, N-acetylglucosamine, galactose, N-acetylgalactosamine, mannose, fucose, xylose and N-acetylneuraminic acid (also known as sialic acid). The sugar group(s) often assist in protein folding or improve proteins' stability. Furthermore, the carbohydrate moieties of glycoproteins and glycolipids are often key components in various intercellular recognition processes, particularly immune responses. Accordingly, presentation of glycoproteins on the exposed surface of a micelle, liposome or membrane can be chosen to target appropriate tissue, inhibit uptake by a particular tissue, and/or induce endocytosis of the micelle. Antibodies, apoproteins, and opsonins are examples of glycoproteins that mediate such responses. Soluble glycoproteins are found in a wide range of biological fluids. For example, the glycoproteins "ovotransferrin", "ovalbumin" and "ovomucoid" are found in certain egg whites (albumen) and the glycoprotein "Glyocophorin A" is commonly found in blood plasma, Similarly, kappa-Casein is found in cow's milk, and the "Tamm-Horsfall" protein is found in the urine of mammals. A wide array of glycoproteins are also found in fruit juice and other plant fluids. Other glycoproteins suitable for use in the context of the present invention include, but are not limited to, human immunoglobulins, such as IgG1; hormones, such as pituitary hormones lutropin (LH), thyrotropin, and pro-opiomelanocortin; proteoglycans, and derivatives thereof. Further examples of suitable glycoprotein hormones include, but are not limited to, follicle stimulating hormone (FSH), luteinizing hormone (LH), thyroid stimulating hormone (TSH), human chorionic gonadotropin (hCG), alpha-fetoprotein, and erythropoietin (EPO).

Proteoglycans are a special class of heavily glycosylated glycoproteins comprised of a core protein with one or more glycosaminoglycan (GAG) chains. The GAG chains are long, linear carbohydrate polymers that are negatively charged under physiological conditions, due to the occurrence of sulphate or uronic acid groups. Proteoglycans are categorized by the nature of their GAG chains, examples of which include, but are not limited to, chondroitin sulfate and dermatan sulfate, heparin and heparin sulfate, keratin sulfate, etc. Examples of large proteoglycans include aggrecan, the major proteoglycan in cartilage, and versican, present in many adult tissues including blood vessels and skin. Small leucine rich repeat proteoglycans (SLRPs) include decorin, biglycan, fibromodulin and lumican.

In addition to being isolated from natural sources, glycoproteins suitable for use in the instant invention can also be synthetically produced or produced by genetically engineered plants and animals, including bacteria and other microbes, in accordance with well-known and conventional techniques.

As used herein, the term "glycan" is synonymous with the term "polysaccharide" as referring to compounds composed of a large number of glycosidically linked monosaccharide units (typically ten or more).

As used herein, the term "glycoside" generically refers to a molecule in which a sugar moiety, typically through its anomeric carbon, is attached to another non-sugar moiety.

When the anomeric carbon is attached via an oxygen atom, the resulting molecule is referred to as an "O-glycoside". Similarly, when the anomeric carbon is attached via an sulfur atom, the resulting molecule is referred to as an "S-glycoside" or "thioglycosides". When the anomeric carbon is attached via a nitrogen atom, the resulting molecule is preferably designated as a "glycosylamine" rather than an "N-glycoside". Illustrative examples of amphiphilic glycosides suitable for use in the context of the present invention include, but are not limited to, chitin, chitosan, cellulose, saponin, and derivatives thereof.

As discussed in greater detail below, the solid state membranes of the present invention may be used to create useful micelles of novel construction. As used herein and in the appended claims, the term "micelle" refers to an aggregate of molecules dispersed in a liquid colloid in which hydrophilic polar components of the molecules orient themselves toward and interact with the aqueous component while hydrophobic, lipophilic and/or nonpolar components are sequestered in the micelle structure. In a typical micelle, the hydrophilic "head" regions contact the surrounding solvent while the hydrophobic "tail" regions are sequestered in the micelle centre. This type of micelle is referred to as a normal phase micelle (oil-in-water micelle). Inverse micelles have the "head" groups at the centre with the "tails" extending out (water-in-oil micelle). Micelles are generally spherical in shape, though other phases, including shapes such as ellipsoids, cylinders, bilayers and objects with irregular or planar surfaces are also possible. The shape and size of a micelle is a function of the molecular geometry of its surfactant molecules and solution conditions such as surfactant concentration, temperature, pH, and ionic strength.

As discussed in greater detail below, membranes and micelles of the present invention are useful for binding target molecules. More particularly, membranes or micelles bearing glycoproteins exhibiting the appropriate binding components (typically sugars) can be used to bind, isolate and extract target molecules from aqueous samples or solutions, particularly those containing disease-causing organisms or other harmful materials such as biotoxins and heavy metals. The aqueous sample assayed is not particularly limited and includes both environmental samples and biological samples. As used herein and in the appended claims, the term "biological sample" includes body fluids, secretions and exudates, examples of which include, but are not limited to, blood, serum, saliva, sputum, urine, plasma, spinal fluid, amniotic fluid, fluids in the gastrointestinal tract, and fluids in the lungs, sweat, breast milk, tears or other lacrimal secretions, pus, and other bodily discharges associated with either normal or diseased conditions.

As discussed in greater detail below, amphiphilic glycosylated membranes and micelles find utility in the fields of diagnostic sensing and pathogen capture. Filters made of cellulose or synthetic fibers coated with the glycosylated amphiphilic membranes of the present invention are particularly useful for removing certain organisms or biotoxins from aqueous solution. Enzymes can be incorporated into the micelles of the present invention to catalyze a variety of chemical reactions in aqueous media. Sensors employing such membranes are also useful in the context of environmental sensing, finding utility in the inspection of foods and in forensic science, for example.

As used herein and in the appended claims, the term "target molecule" encompasses both endogenous biological entities, such as peptides, proteins, hormones, oligonucleotides, nucleic acid molecules, (e.g., RNA and/or DNA), cellular components, and particulate analytes, as well as foreign materials, including, but not limited to, pathogens, toxins, drugs, contaminants, pollutants, chemical substances, and analytes. In certain instances, the presence and/or level of target molecule in a sample will correlate with a particular disease or disorder (e.g., a bacterial infection, heavy metal poisoning, cancer, etc.).

As discussed in greater detail below, the membranes and micelles of the present invention find particular utility in the context of pathogen capture. As used herein and in the appended claims, the term "pathogen" encompasses any natural or bioengineered disease-producing agent, particularly viruses, bacteria, and other microorganisms (e.g., amoeba, protozoans, etc.). The membranes and micelles of the present invention also find utility in the context of environmental detection and detoxification, for example in the removal of heavy metals. As used herein and in the appended claims, the term "heavy metal" refers to a metal having a relatively high density (i.e., a specific gravity greater than 4.0, more preferably greater than 5) or a relatively high atomic weight (i.e., falling on the periodic table between copper and bismuth). Excessive levels of heavy metals are known to be detrimental to living organisms. Examples of heavy metals associated with serious illness (e.g., heavy metal poisoning) include, but are not limited to, lead, mercury, copper, cadmium, manganese, aluminum, beryllium, molybdenum, vanadium, strontium, zinc, and iron.

As discussed in greater detail below, the glycosylated amphiphilic membranes of the present invention find utility as coatings for medical devices. In the context of the instant invention, the term "medical device" encompasses both devices intended for limited introduction (for example angioplasty catheters) as well as devices intended for long term insertion (for example cardiac pacemakers). More particularly, as used herein and in the appended claims, the term "medical device" refers to any apparatus, appliance, instrument, implement, material, machine, contrivance, implant, in vitro reagent, or other similar or related article including a component party or accessory which is intended for the diagnosis, prevention, monitoring, treatment or alleviation of disease, injury or handicap. It further encompasses any article intended to affect the structure or function of the body of humans or other animals, and which does not achieve its principal intended action in or on the body by pharmacological, immunological or metabolic means, but which may be assisted in its function by such means.

II. Constructing Embodiments of the Present Invention

Central to the instant invention is the discovery that many amphiphilic molecules, particularly glycolipids and glycoproteins endogenous to plant and animal tissue fluids, spontaneously aggregate at the interface between certain aqueous solutions and certain non-polar liquids to form a flexible membrane. The lipophilic components of the molecules adhere, through non-covalent hydrophobic interactions, to molecules of oil or other non-polar liquids and present their hydrophilic moieties toward the aqueous phase to produce a membrane, which, when agitated (e.g., rolled, shaken, or forced through a filter), stretches and breaks into closed vesicles or micelles. This technology is discussed in detail in U.S. Pat. Nos. 5,824,337 (Mullen), 6,528,092 (Mullen), and 7,148,031 (Mullen), the contents of which are incorporated by reference herein in their entirety. Accordingly, micelles that embody this technology are often referred to herein as "Mullen micelles".

In many instances the glycoprotein membrane and the micelles produced by association of non-polar liquids with glycoproteins are mechanically and chemically more stable than those formed from phospholipids. For example, unlike phospholipids based liposomes and micelles, the polar surfaces of the glycoprotein micelles do not fuse easily and are quite stable in aqueous media. They are able to retain their shape and hold their contents and are very resistant to destruction. For example, they can be selectively extracted using physical means such as separatory funnel or syringe which, in turn, enables the creation of micelle populations that are relatively uniform in size. In addition, the glycoprotein micelles may be used as carriers for substances that are not, when used alone, capable of forming relatively stable micelles (e.g., lipids, lipophilic, and lipid-like moieties).

Depending upon the amphiphilic compound utilized, the Mullen micelles can be kept for months at room temperature in sterile aqueous solution and indeed in some instances can, under very restrictive conditions, be dried and subsequently rehydrated. However, the dried membranes tend to lose their elasticity and are quite fragile. If fact, when the aqueous solvent is evaporated, only a diaphanous, brittle monolayer of glycoprotein remains. It is accordingly an object of the present invention to provide a means for stabilizing the micelle membrane, so as to facilitate the long term storage and convenient transport of both membranes and micelles formed therefrom. To that end, the present invention utilizes a non-polar material, first in a liquid form to first initiate membrane formation, then, in a solid form in which the hydrophobic "tails" of the amphiphilic molecule are embedded in or linked to its surface while the hydrophilic "heads" protrude therefrom so as to present useful properties to the surrounding environment. The transformation from liquid to solid, either through thermal, chemical or radiative means, results in "locking" of the amphiphilic molecule to non-polar material. More particularly, the hydrophobic ends of the amphiphilic compounds are affixed to the surface of the solid, either through mechanical, chemical or physical means. The resulting membrane or film remains stable even if the polar solvent is removed, thereby allowing the hydrophilic components of the amphiphilic compounds to present useful properties at the surface of the solid material.

The amphiphilic molecules that form the surface of the membranes and micelles of the present invention can vary in form and source. The amphiphilic molecules need only to act as surfactants in the presence of the selected polar solvent and the fluid state of the non-polar substrate, be it wax, plastic, fat, polymer or other hydrocarbon.

The substrate material can also vary greatly. The substrate needs to be non-polar (or sufficiently non-polar) in the fluid form to permit formation of micelle or micelle-like alignment of the amphiphilic compounds at the interface with the polar solvent. Upon solidification, the solid material must provide a mechanical or chemical bond such that the amphiphilic material remains oriented with the hydrophilic end presented to the surrounding environment and thus exhibiting useful properties.

In preparation of the construct of this invention, the solid or solid-film material may be allowed to solidify without agitation, resulting in a relatively flat or contour conforming surface. If the non-polar material, for example a wax or plastic polymer, when in liquid form is agitated in the polar solvent in the presence of an amphiphilic compound at the proper concentration and temperature, then micelle structures spontaneously will form. These structures can be preserved in the transition of the non-polar materials from liquid to a solid state.

As with fluid micelles, the size of the solid micelle-like structures can be influenced during formation through the degree of agitation, concentration of amphiphilic compound and selection of amphiphilic compound.

Accordingly, a typical method for a making a glycosylated amphiphilic membrane or film of the present invention generally includes the following steps:

(a) providing a polar solvent having sufficient quantities of one or more glycosylated amphiphilic molecules dissolved therein;
(b) exposing the polar solvent to a non-polar liquid, the non-polar liquid being immiscible in said polar solvent;
(c) allowing the glycosylated amphiphilic molecules to align so as to form a membrane that separates the polar solvent from the non-polar liquid; and
(d) inducing transformation of the non-polar liquid to a corresponding non-polar solid, for example, through the application of thermal, chemical or radiative stimulus, such that the hydrophobic tail ends of the amphiphilic molecule become embedded in or chemically or mechanically linked to the non-polar substrate while the hydrophilic tail ends project from the substrate to provide the membrane with a functionally active surface.

The polar solvent may optionally be removed so as to yield a dry solid state film. As mentioned above, depending upon the desired membrane form, shape and structure, it may be further desirable to manipulate the reactants prior to, during or subsequent to transition. For example, by controlling the temporal component of the transition process (for example, speeding up the transition process through rapid cooling of the non-polar liquid), one can drive the production of micelle constructs having particular size or geometry. Alternatively, agitating the film prior to or during transition will result in the formation of micelle-like constructs.

The structures of the present invention have been shown to have a level of stability after removal of the non-polar solvent. This is considered a very useful property in allowing preservation of the material of the invention. Lack of moisture will decrease the likelihood of biological attack during storage. Additionally, removal of moisture allows for storage of the material at reduced temperature without the risk of ice crystals damaging the biological compounds.

Fluid micelles and micelle-like structures have an inherent problem of reduced dimensional stability when exposed to high-shear conditions such as in a turbulent non-polar solvent flow. The solid micelles and micelle-like structures of this invention are more stable in those conditions and thus are more suited to applications involving turbulent flow, for example in the context of environmental filters.

III. Utilities of the Present Invention

The glycosylated amphiphilic membranes and micelles of the present invention have a wide range of utilities, ranging from environmental sensing to pathogen capture. The membranes of the present invention are particularly useful for extracting target molecules, for example, contaminating substances such as pathogens, pollutants, and the like, from a particular sample. A typical method for extracting a target molecule of interest from a particular sample using a glycosylated amphiphilic membrane or film of the present invention generally includes the following steps:

(a) exposing the sample to a solid state membrane or membrane coated implement or device;
(b) allowing a sufficient time for the functional groups present on the hydrophilic tail end of the glycosylated amphiphile to bind target molecules present in the sample; and
(c) removing or separating the membrane, having target molecules bound thereto, from the sample.

In certain instances, it may be desirable to subject the sample to a force which promotes contact between the target molecule and the membrane. Illustrative examples of such forces include, but are not limited to, mechanical acceleration, centrifugal force, electrical force, magnetic force, hydraulic force and various other means for agitation.

Upon removal from the sample, the membrane may then be analyzed for the presence of target molecule using any number of commercially available detection and measurement technologies (e.g., PCR, immunoassays, DNA microarrays, protein microarrays, etc.). In certain instances, the amount of target molecule bound to the membrane may be used to estimate the amount of target molecule present in the sample. Such levels can also be used to diagnose the presence of a disease condition (e.g., a bacterial infection, cancer, etc.)

Since the technology can exhibit both the properties of binding to pathogens and physical manifestation in a microscopic form (micelle construct), the instant technology also finds utility as an alternative to Hemagglutination, wherein pathogens are detected through their ability to bind to multiple red blood cells at once, resulting in visible agglutination of the cells.

In that the membranes of the instant invention find application in a number of divergent environments, the structure and form of the inventive membrane is not particularly limited. For example, the membranes of the present invention may take the form of a biological or environmental filter or sensor, such as a microarray or biochip sensor having specificity (via the functional ends of the embedded glycosylated amphiphile) for one or more proteins, antibodies, tissues, or chemical substances. Alternatively, in the context of pathogen capture and filtration, it may be beneficial to coat a vessel or pipe or filter media contained within with a membrane of the present invention having binding specificity for one or more target molecules, for example glycoproteins exhibiting sugars specific to a particular class of pathogens, with the intent of placing a liquid sample of interest in the pipe in contact with said membranes. Accordingly, in addition to serving as a source for micelle construction, the membranes of the present invention, surface-embedded with glycosylated amphiphiles, find utility both as singular solid state materials and as film coatings on other materials or for other devices.

In the context of the instant invention, the "other" material on which the membrane is disposed may serve as structural or geometric support or, alternatively, may address thermal or density issues. Alternatively, the "other" material may comprise a useful device or implement, for example, a sample containing vessel, pipe, tube, or the like. For example, in those instances where the sample is in the form of a continuous fluid stream, a glycosylated amphiphilic membrane of the present invention may be anchored or adhered to a stream contacting surface of a vessel through which the fluid stream sample is passed. In other embodiments, it may be desirable to adhere a membrane coating of the instant invention to the walls of a centrifuge, such that contaminating substances present in the sample are accelerated towards and then captured by the hydrophilic moieties present on the surface of the membrane, the particular hydrophilic moieties having binding specificity for target contaminants of interest. In further embodiments, the useful implement may comprise a medical device that would benefit from biological properties displayed by the glycosylated amphiphilic membrane of the present invention.

Medical devices, particularly implantable medical devices, often fail as a result of a biological organism's reaction to its introduction. In many instances, the reaction arises from the identification of the introduced device as "foreign" and involves subsequent protective attempts by the organism's immune system to remove, sequester or destroy the perceived injurious stimuli and initiate the healing process. An example of such a reaction is transplant rejection, which occurs when the immune system of a recipient of a transplant attacks the transplanted organ or tissue. In addition, non-specific binding (NSB) of proteins at medical implant surfaces is believed to be at least partially responsible for triggering the foreign body response, which in turn can lead to device failure or rejection. This "biofouling" is also blamed for device infection incidence, thrombosis, and sensor deterioration over time in vivo.

Accordingly, in the context of medical devices, it is highly advantageous to be able to mask the foreign nature of the device so as to prevent the rejection process. One means to achieve this goal involves coating the medical device with a biocompatible material that minimizes or substantially eliminates such negative reactions. In addition, functionally inert surface coatings for medical implant devices can effectively limit host rejection of the medical implant device through attached ligands, incorporated drugs, and reduced NSB responsible for biofouling of such devices in or ex vivo. The glycosylated amphiphilic membranes of the instant invention find particular utility as such biocompatible coatings. In that many glycosylated moieties are native to living systems, they are less likely to trigger immune response. Accordingly, solid state membranes expressing such endogenous glycosylated amphiphiles (or functionally active fragments or derivatives thereof) will mimic endogenous tissues and thus be recognized by the immune system as "self" rather than "foreign". Such "biomimetic" membranes are particularly useful as antigenicity reducing coatings for medical devices.

In certain instances, in the interest of further reducing potential immune response, it may be desirable to construct a membrane of the instant invention using a glycosylated amphiphile isolated, extracted or derived from an intended recipient or, alternatively, an antigen-matched donor. While an ideal donor would be an HLA-identical sibling, alternative donors include an HLA-phenotypically matched unrelated donor (MUD), a partially mismatched related donor (PMRD) or a cord blood donor (CBD), who can be a phenotypically matched or mismatched related or unrelated donor.

Medical devices that would benefit from such antigenicity reducing coatings include both temporary implants (i.e., devices intended for limited introduction, for example angioplasty catheters) and more permanent implants (i.e., devices intended for long term insertion, for example cardiac pacemakers). Examples of medical devices contemplated by the instant invention include, but are not limited to, needles, catheters (e.g., intravenous, urinary, and vascular catheters), stents, shunts (e.g., hydrocephalus shunts, dialysis grafts), tubes (e.g., myringotomy tubes, tympanostomy tubes), implants (e.g., breast implants, intraocular lens), prosthetics, and artificial organs, as well as cables, leads, wires, and electrodes associated therewith (e.g., leads for pace makers and implantable defibrillators, bipolar and monopolar RF electrodes, vascular guidewires). Also contemplated are devices such as wound dressings, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, vascular supports, and other body contacting devices that may benefit from enhanced biocompatibility.

In addition to enhancing the biocompatibility of medical devices, the solid state membranes of the instant invention, more particularly the functionally active glycosylated moieties provided on the surface thereof, may possess analytic, diagnostic and/or therapeutic utility. For example, the glycosylated amphiphilic molecule selected may have a binding specificity for a target molecule of biological or medical interest. Glycosylated amphiphilic membranes so fabricated can be used to capture and extract such materials, either in vivo or ex vivo. Examples of target molecules of biological or medical interest include, but are not limited to, biological entities such as hormones, proteins, nucleic acid molecules, (e.g., RNA and/or DNA), circulating cells, and particulate analytes of biological origin that serve as diagnostic indicia or biomarkers of disease, for example cancer. Also contemplated are foreign materials, particularly biohazardous materials, such as contaminants, drugs, toxins, heavy metals, pathogens and the like.

In certain instances, the glycosylated amphiphilic membranes of the present invention (as well as medical devices formed therewith) can serve not only to detect the presence of the target molecule but also effectively remove it from (i.e., detoxify) the sample. For example, when the target molecule of interest is a heavy metal, such as lead, mercury, copper, or the like, the selected glycosylated amphiphile may act as a chelating agent that binds the heavy metal and effectively eliminates it from circulation.

The glycosylated amphiphilic membranes of the instant invention also find utility in the areas of environmental detection and detoxification. For example, the inventive membranes may take the form of a filter for capturing target molecules that may be present in an environmental sample, such an entering or exiting water source (e.g., an agricultural feed trough or runoff ground water). By positioning a filter with a functionally active surface in contact with a stationary or flowing water source, target molecules present in the source become bound to the hydrophilic ends of the glycosylated amphiphiles. In this manner, the target molecules can effectively removed from the source and safely transported to a laboratory setting. Alternatively, the filters may be provided with a means for real-time detection and measurement of target molecule binding. Real-time detection may involve analysis of a change in a readily measurable parameter, for example changes in optical spectra (e.g., fluorescence, color change), electrical activity, electrical field (e.g., conductance), or magnetic field.

Depending upon the detection methodology utilized, it may be desirable to transport the membranes to a separate location, such as a laboratory setting, for analysis. In that the target molecule is firmly bound to the membrane, it no longer constitutes a danger to either the surrounding environment or to the analyst (i.e., safe handling through conjugation). Accordingly, a technician may opt to either assess the target molecule in situ, while bound to the membrane or, alternatively, may opt to unbind it from the filter, for example with the help of a lysing solution or the like. In the context of hazardous materials, such as pathogens, the lysing solution is likely to effectively kill the pathogen, thereby eliminating the dangers associated with conventional detection methods that utilize live pathogens.

Hereinafter, the present invention is described in more detail by reference to the Examples. However, the following materials, methods and examples only illustrate aspects of the invention and in no way are intended to limit the scope of the present invention. As such, methods and materials similar or equivalent to those described herein can be used in the practice or testing of the present invention.

EXAMPLES

Example 1

Figure 1:
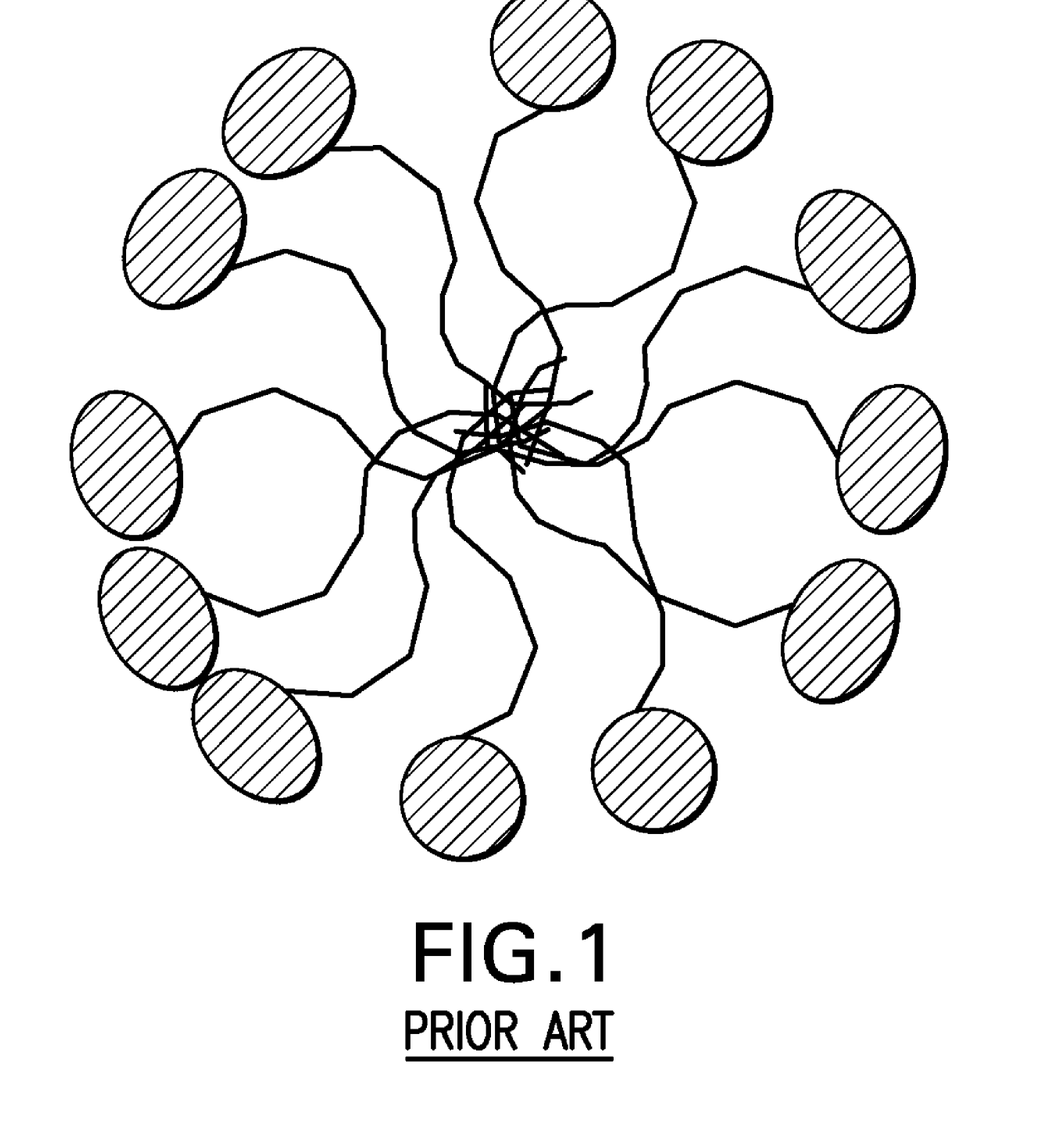
Figure 2:
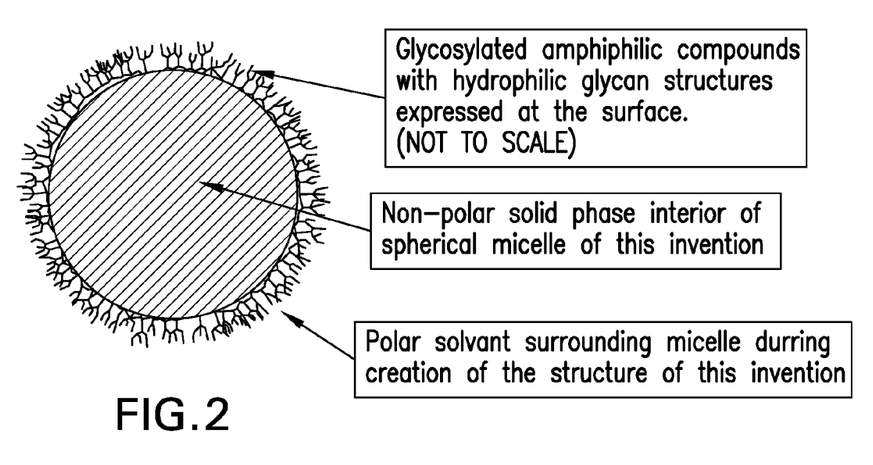
Figure 3:
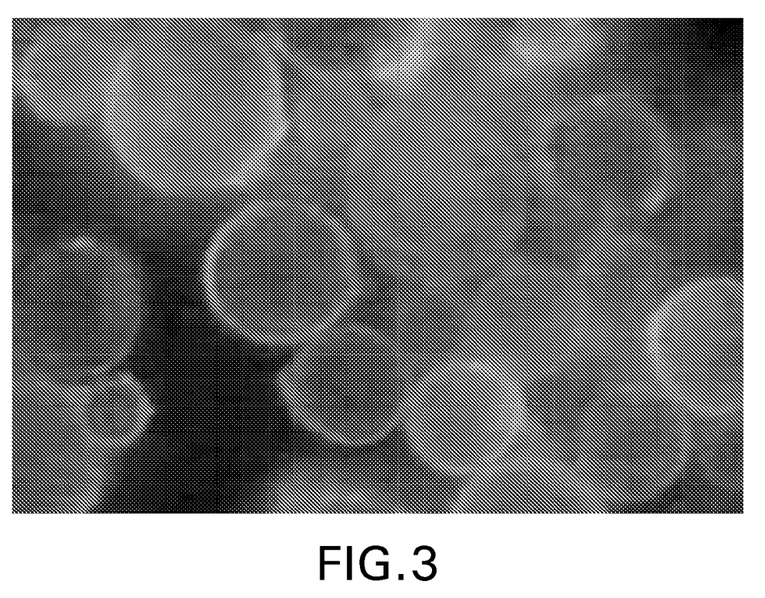

Paraffin wax (100 ml) was melted at a temperature of 70° C. Chicken egg white (50 ml) was dissolved in distilled water (400 ml) and the resultant mixture was filtered and then heated to 70° C. The melted wax was added to the egg white mixture, which was then agitated and quickly cooled to a temperature below 40° C. through the addition of chilled water. Glycoproteins recovered from chicken egg whites were embedded in the surface of paraffin wax in a manner that the wax formed micelles in the diameter range of 0.001 to 4 mm. The size range of glycoprotein covered spheres was found to be dependent in part on the degree of agitation just prior to the cooling step. The resultant spherical structures (i.e., micelles) were dried, rewetted, and exposed to fluorescent lectins. The lectins were found to successfully bind to the sugars on the embedded glycoproteins (FIG. 3).

Example 2

A solution of yeast invertase and low density polyethylene (LDPE) was heated in an agitated pressure reactor to a temperature of 120° C. The solution was then cooled through rapid depressurization of the reactor followed by the addition of chilled water. LDPE micelles having surface embedded glycoproteins recovered from yeast invertase were thus formed, the micelles having a diameter ranging from 0.1 to 4 mm. The resultant micelles were dried, rewetted, and exposed to fluorescent lectins. The fluorescent lectins were observed to have successfully bound to the sugars on the embedded glycoproteins.

Example 3

A water solution containing Tamm-Horsfall glycoproteins and carnauba wax flakes was heated to 98° C., until the carnauba wax melted and formed a continuous layer at the surface of the water solution. The solution was then allowed to cool to room temperature, at which point a solidified carnauba wax film was formed. The film was removed from the top of the remaining solution, rinsed under running water for 3 minutes and then allowed to dry. The resulting flat film comprised Tamm-Horsfall glycoproteins embedded in the surface of carnauba wax.

Example 4

Glycoproteins recovered from cranberries were embedded in the surface of paraffin wax in a manner analogous to that of Example 3. The wax formed micelles had a diameter ranging from 0.001 to 0.1 mm. A similar process was repeated without the glycoproteins present and the wax failed to form micelles.

Example 5

Figure 4:
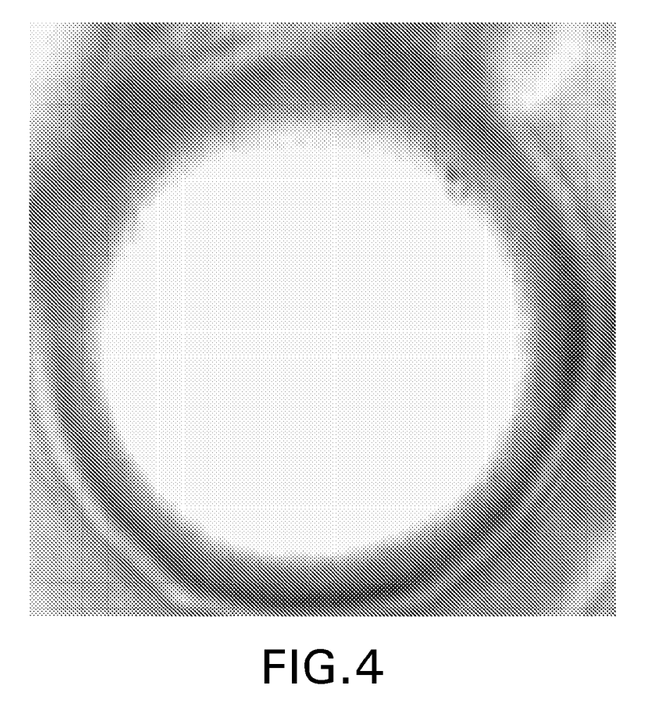

Paraffin wax micelles having a surface embedded with the glycoproteins of yeast invertase can be made according to any of the processes above. The reactivity of the micelles was assayed by exposing them to a solution containing *Salmonella* and *E. coli* and agitating the mixture for a period of 15 minutes. The solution was then stained using crystal violet. The wax micelles were then rinsed in fresh water and observed under the microscope. Bacteria were observed to be bound to the surface of the wax micelles (FIG. 4).

Example 6

Wax micelle beads of a diameter between 0.5 mm and 1.5 mm can be placed in a cylindrical tube, 15 mm in diameter by 80 mm long. Filter mesh with 0.25 mm openings is then placed at either end of the tube to contain the beads. A solution containing *Salmonella* can be pumped through the tube. A rinse solution is then pumped through the tube for 1 minute. The tube is removed and a lysing solution is then placed in the tube. The lysed solution is drained from the tube and subsequently analyzed for *Salmonella* using PCR. The PCR can positively detect the presence of *Salmonella*.

Example 7

The interior walls of a cylindrical vessel of approximately 3" in diameter can be coated with a yeast invertase in paraffin film of the instant invention. The cylinder is then filled with a *Salmonella* bearing solution and rotated on its cylindrical axis for about 15 minutes at 10,000 rpm. The vessel is then filled and emptied of a rinse solution for a total of five cycles. A section of vessel wall is stained with crystal violet and then examined under a microscope. *Salmonella* is detected binding to the membrane on the vessel wall.

Industrial Applicability

The solid state films and membranes of the present invention, formed from the spontaneous aggregation and specific alignment of glycosylated amphiphilic molecules at the interface between a polar solvent and a non-polar liquid, can be used to produce relatively robust and stable micelles having improved long term storage capacity. In that the membranes and micelles of the present invention, having surface embedded glycosylated amphiphiles, present useful biological properties to the surrounding environment, they find particular industrial applicability in the areas of environmental sensing, pathogen capture, diagnostic assessment, and therapeutic detoxification.

All patents and publications mentioned herein are incorporated by reference in their entirety. Nothing herein is to be construed as an admission that the invention is not entitled to antedate such disclosure by virtue of prior invention.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention.

Other advantages and features will become apparent from the claims filed hereafter, with the scope of such claims to be determined by their reasonable equivalents, as would be understood by those skilled in the art. Thus, the invention is intended to be defined not by the above description, but by the following claims and their equivalents.

What is claimed:

1. A method of extracting target molecules from a sample comprising the step of:
   (a) providing a dryable solid state film having at least one functionally active surface with binding affinity for a target molecule, said film comprising a non-polar solid substrate having upper and lower surfaces, said substrate having directly affixed thereto a plurality of glycosylated amphiphilic molecules in a stable amphiphilic alignment, each of which comprise a hydrophobic tail end and a hydrophilic head end provided with one or more functional groups, wherein the hydrophobic tail ends are embedded in or chemically linked to the upper surface of said non-polar solid substrate and the functional groups of the hydrophilic tail ends have binding affinity for a target molecule and project from said upper surface so as to provide at least one surface of said film with binding activity;

(b) exposing said sample to the solid state film of part (a), wherein the functional groups present at the hydrophilic tail end of the glycosylated amphiphilic molecules have a binding affinity for a target molecule;

(c) allowing sufficient time for said functional groups to bind target molecules present in said sample; and (d) removing or separating said film, to which said target molecules are bound, from said sample.

2. The method of claim 1, wherein said target molecule is a natural or bioengineered pathogen, selected from the group consisting of microbes, viruses and toxins.

3. The method of claim 1, wherein said target molecule comprises a heavy metal.

4. The method of claim 1, further comprising the step of analyzing the film or a material extracted from the film for the presence of target molecule.

5. The method of claim 4, wherein said analysis step utilizes a detection technology selected from the group consisting of PCR, immunoassays, DNA microarrays, protein microarrays, and optical recognition.

6. The method of claim 1, further comprising the step of calculating the amount of target molecule present in the sample based on the amount of target molecule bound to the film.

7. The method of claim 1, wherein said sample is a biological sample selected from the group consisting of blood, serum, saliva, sputum, urine, plasma, spinal fluid, amniotic fluid, fluids in the gastrointestinal tract, and fluids in the lungs, sweat, breast milk, tears or other lacrimal secretions, pus, and other bodily discharges associated with either normal or diseased conditions.

8. The method of claim 1, wherein said sample comprises a continuous fluid stream and said target molecule comprises a natural or bioengineered pathogen suspected of being present in said fluid stream, further wherein said solid state film is adhered to a stream contacting surface of a vessel through which said fluid stream sample is passed.

9. The method of claim 1, wherein the sample is subjected to a force which promotes contact between the target molecule and the membrane, said force selected from the group consisting of agitation, mechanical acceleration, centrifugal force, electrical force, magnetic force, and hydraulic force.

10. The method of claim 1, further comprising the steps of (d) subjecting the film to which target molecules are bound to a lysing agent that effectively separates the target molecules from the film and (e) detecting the presence of separated target molecules.

11. The method of claim 1, wherein said sample is a biological sample and said steps of exposing and binding occur in vivo.

12. The method of claim 1, wherein said sample is a biological sample and said steps of exposing and binding occur ex vivo.

13. The method of claim 11, wherein said target molecule comprises a natural or bioengineered pathogen.

* * * * *